United States Patent
Mashimo et al.

(10) Patent No.: US 11,135,217 B2
(45) Date of Patent: Oct. 5, 2021

(54) MANUFACTURING PROCESS OF FORMULATION HAVING IMPROVED CONTENT UNIFORMITY

(71) Applicant: Shionogi & Co., Ltd., Osaka (JP)

(72) Inventors: Akira Mashimo, Hyogo (JP); Shunji Ichio, Hyogo (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 16/473,435

(22) PCT Filed: Dec. 26, 2017

(86) PCT No.: PCT/JP2017/046614
§ 371 (c)(1),
(2) Date: Jun. 25, 2019

(87) PCT Pub. No.: WO2018/124062
PCT Pub. Date: Jul. 5, 2018

(65) Prior Publication Data
US 2020/0147074 A1 May 14, 2020

(30) Foreign Application Priority Data
Dec. 26, 2016 (JP) .............................. JP2016-250513

(51) Int. Cl.
*A61K 31/485* (2006.01)
*A61K 9/16* (2006.01)

(52) U.S. Cl.
CPC .......... *A61K 31/485* (2013.01); *A61K 9/1611* (2013.01); *A61K 9/1617* (2013.01); *A61K 9/1623* (2013.01); *A61K 9/1652* (2013.01)

(58) Field of Classification Search
CPC .. A61K 31/485; A61K 9/1611; A61K 9/1617; A61K 9/1623; A61K 9/1652
See application file for complete search history.

(56) References Cited

U.S. PATENT DOCUMENTS

| 2008/0317863 | A1* | 12/2008 | Nystrom | ................ | A61K 9/006 424/491 |
|---|---|---|---|---|---|
| 2013/0071477 | A1 | 3/2013 | Fischer | | |
| 2013/0231485 | A1 | 9/2013 | Tamura et al. | | |
| 2015/0150287 | A1 | 6/2015 | Kragh et al. | | |
| 2015/0216804 | A1 | 8/2015 | Mashimo et al. | | |

FOREIGN PATENT DOCUMENTS

| EP | 1 889 848 | | 2/2008 |
|---|---|---|---|
| EP | 2 639 234 | | 9/2013 |
| EP | 2 851 075 | | 3/2015 |
| JP | 11-147819 | | 6/1999 |
| JP | 2000-7583 | | 1/2000 |
| JP | 2008-94751 | | 4/2008 |
| WO | 2006/085101 | | 8/2006 |
| WO | 2008/068471 | | 6/2008 |
| WO | 2008/072354 | | 6/2008 |
| WO | 2013/041851 | | 3/2013 |
| WO | 2013/080271 | | 6/2013 |
| WO | WO 2013090452 | * | 6/2013 |
| WO | 2013/157754 | | 10/2013 |
| WO | 2013/182518 | | 12/2013 |
| WO | 2015/016256 | | 2/2015 |

OTHER PUBLICATIONS

Sun et al. (particle size specification for solid forms) 2010.*
English translations of International Preliminary Report on Patentability and Written Opinion dated Jul. 11, 2019 in International (PCT) Application No. PCT/JP2017/046614.
International Search Report dated Feb. 23, 2018 in International Application No. PCT/JP2017/046614.
"Study on Dynamics of Electromagnetic Particles in Electromagnetic Field and Application to Imaging Technology", Doctoral dissertation (Nobuyuki Nakayama, Feb. 2003).

* cited by examiner

*Primary Examiner* — Shirley V Gembeh
(74) *Attorney, Agent, or Firm* — Wenderoth, Lind & Ponack, L.L.P.

(57) ABSTRACT

The present invention offers the manufacturing method of the solid formulation wherein the standard deviation of the active ingredient content in the solid formulation becomes 5% or less by mixing the excipients which have a median particle size of 15 or more times, preferably 20 times or more to the median particle size of an active ingredient.

18 Claims, No Drawings

MANUFACTURING PROCESS OF FORMULATION HAVING IMPROVED CONTENT UNIFORMITY

TECHNICAL FIELD

The present invention is a manufacturing method of solid formulations comprising a process of mixing the active ingredient and an excipient with a median particle size of 15 times or more, preferably 20 times or more, relative to the median particle size of the said active ingredient. By taking the said manufacturing method, the standard deviation of content on the active ingredient in the formulation can be 5% or less.

BACKGROUND ART

Content uniformity is a problem in the case of formulations containing a low content of active ingredient, especially in the case of tablets. That is, it is difficult to prepare tablets with good content uniformity, even if the tablets are produced by the direct compression method, in which the active ingredient and additive with low content are simply mixed and tableted. When a tablet containing a low content of active ingredient need to be produced by direct compression method, the additive need to be mixed in several steps in small amounts with the active ingredient, and the manufacturing process becomes complicated. Therefore, in the case of tablets with such low-content active ingredients, the active ingredient and additive are often granulated to produce the tablet, once the granule is produced, and the granule is pressed to produce the tablet.

When granules are produced, active ingredients and additives are often mixed, granulated with solvents such as water, and then dried for production. However, some active ingredients can be degraded by solvent such as water. In addition, there is a possibility that the crystal form of the active ingredient is changed by solvents such as water or the like, and the active ingredient may be decomposed by the drying process of the granule.

As described above, when the active ingredient is degraded by a solvent such as water, it is not preferable to produce the tablet by the granule compression method, and the direct compression method without using a solvent such as water is preferable. Therefore, a direct compression method, which can produce tablets with good content uniformity and, which does not complicate the manufacturing process is desired.

Patent Literatures 1 and 2 are disclosed as the literature of tablets produced by the direct compression method with a low content of active ingredient. However, in these documents, the particle size of the active ingredient alone is reduced, or the particle size of the additive alone is reduced to make the content uniformity good, but it is not always possible to achieve the objective content uniformity.

Active ingredients that exert medicinal effects at low content include 6,7-unsaturated-7-carbamoylmorphinane derivatives, which are side effect reducing agent of agonists of opioid receptors. Patent Literatures 3 and 4 disclose the said compound and the manufacturing method of producing the said compound. Also, in Patent Literature 5, a formulation containing the said compound is disclosed. However, no content uniformity is disclosed in Patent Literatures 3 to 5.

CITATION LIST

Patent Literature

[Patent Literature 1] International Publication No. 2008/072354
[Patent Literature 2] Japanese Patent Laid-Open No. 2015-530355
[Patent Literature 3] International Publication No. 2006/126637
[Patent Literature 4] International Publication No. 2012/063933
[Patent Literature 5] International Publication No. 2013/172297

SUMMARY OF INVENTION

Problems to be Solved by the Invention

The problem of the present invention is to provide a manufacturing method of a formulation which is simple and has high content uniformity of the active ingredient by the direct compression method, and the formulation.

Means for Solving the Problems

In order to solve the above-mentioned problems, the inventors conducted intense research, focusing on the difference in the median particle size between the active ingredient and the excipient, and found that a solid formulation with a standard deviation of the active ingredient content in the formulation within 5% can be produced by mixing excipients with a median particle size of 15 times or more for the median particle size of the active ingredient, even if the amount of the active ingredient is small, leading to the completion of the present invention (Hereinafter, a formulation thus accomplished by the present invention is sometimes referred to as the "present formulation").

Specifically, the present invention relates to the following:
(1) A process for manufacturing a solid formulation characterized in including a step of mixing an active ingredient and an excipient which has a median particle size of 15 times or more to the median particle size of the said active ingredient, wherein the standard deviation of content in the active ingredient is 5% or less;
(2) the process for manufacturing a solid formulation according to (1) above, characterized by including the following steps;
(i) a step of mixing the active ingredient, and the excipient which has the median particle size of 15 times or more to the median particle size of the said active ingredient,
(ii) a step of compression molding the said mixture by the method of direct compression or dry granulation;
(3) the process for manufacturing a solid formulation according to above (1) or (2) above, wherein the median particle size of the excipient is 20 times or more to the median particle size of the active ingredient;
(4) the process for manufacturing a solid formulation according to any one of (1) to (3) above, wherein the standard deviation of content on the active ingredient is 3% or less in the formulation;
(5) the process for manufacturing a solid formulation according to any one of (1) to (4) above, wherein the content of the active ingredient is 10% or less by weight in the formulation;
(6) the process for manufacturing a solid formulation according to (5) above, wherein the content of the active ingredient is 5% or less by weight in the formulation;
(7) the process for manufacturing of a solid formulation according to (5) above, wherein the content of the active ingredient is 1% or less by weight in the formulation;

(8) the process for manufacturing of a solid formulation according to any one of (1) to (7) above, wherein the content of the excipient is 50 to 99.99% by weight in the formulation;

(9) the process for manufacturing a solid formulation according to (8) above, wherein the content of an excipient is 60 to 99.99% by weight in the formulation;

(10) the process for manufacturing a solid formulation according to (8) above, wherein the content of an excipient is 70 to 99.99% by weight in the formulation;

(11) the process for manufacturing a solid formulation according to any one of (1) to (10) above, wherein the median particle size of the active ingredient is 10 μm or less;

(12) the process for manufacturing a solid formulation according to any one of (1) to (10) above, wherein the median particle size of the active ingredient is 8 μm or less;

(13) the process for manufacturing a solid formulation according to claim 11, wherein the median particle size of the active ingredient is 5 μm or less;

(14) the process for manufacturing a solid formulation according to any one of (1) to (13) above, wherein the median particle size of the excipient is 30 μm or more;

(15) the process for manufacturing a solid formulation according to (14) above, wherein the median particle size of the excipient is 45 μm or more;

(16) the process for manufacturing a solid formulation according to (14) above, wherein the median particle size of the excipient is 60 μm or more;

(17) the process for manufacturing a solid formulation according to (11) or (14) above, wherein the median particle size of the active ingredient is 10 μm or less and the median particle size of the excipient is 30 μm or more;

(18) the process for manufacturing a solid formulation according to any one of (1) to (17) above, wherein the content of the active ingredient in the formulation is 1% or less, the median particle size of the said active ingredient is 5 μm or less, the median particle size of the excipient is 60 μm or more, and characterized in including the step of mixing the active ingredient and the excipient which has the median particle size of 20 times or more to the median particle size of the said active ingredient, wherein the standard deviation of content in the active ingredient is 3% or less in the formulation;

(19) the process for manufacturing a solid formulation according to (18) above, wherein the content of the active ingredient in the formulation is 1% or less, the median particle size of said active ingredient is 5 μm or less, the median particle size of the excipient is 60 μm or more, and characterized in including (i) the step of mixing the active ingredient and the excipient which has the median particle size of 20 times to the median particle size of the said active ingredient, (ii) the step of compression molding the said mixture by the method of direct compression or dry granulation;

(20) the process for manufacturing a solid formulation according to any one of (1) to (19) above, which contains an unstable compound for water as the active ingredient;

(21) the process for manufacturing a solid formulation according to any one of (1) to (20) above, containing a compound represented by the formula (IA):

[Formula 1]

(IA)

its pharmaceutically acceptable salt, or a solvate thereof as the active ingredient;

(22) the process for manufacturing a solid formulation according to (21) above, containing p-toluene sulfonic acid salt, acetate or hydrochloride salt of the compound represented by the formula (IA), or a solvate of the salt as the active ingredient;

(23) the process for manufacturing a solid formulation according to any one of (1) to (22) above, containing sugar or sugar alcohol as the excipient;

(24) the process for manufacturing a solid formulation according to (23) above, containing D-mannitol as the excipient;

(25) the process for manufacturing a solid formulation according to any one of (1) to (24) above, wherein the solid formulation is one or more selected from the group consisting of tablet, granule, powder and capsule;

(26) A solid formulation produced by the process for manufacturing, according to any one of (1) to (25) above;

(27) A solid formulation containing a unstable compound, its pharmaceutically acceptable salt or its solvate as an active ingredient to water and a excipient, wherein the content of the active ingredient is 1% or less and the standard deviation of content on the active ingredient is 3% or less in the formulation;

(28) The solid formulation according to (27) above, wherein the content of the excipient is 70 to 99.99% by weight in the formulation;

(29) The solid formulation according to (27) or (28), containing a compound represented by the formula (IA):

[Formula 2]

(IA)

its pharmaceutically acceptable salt or a solvate thereof as the active ingredient.

Effect of the Invention

According to the present invention, the content uniformity of the active ingredient is high. A result of the determination on the content of the solid formulations of the present invention shows that the standard deviation of the content of the active ingredient is 5% or less, preferably 3% or less.

Mode for Carrying Out the Invention

In the present formulation, the active ingredient may be used in a medicine. Especially, active ingredients with a small content of active ingredients in the formulation or those that are unstable to water can exert the effects of the present invention. Here, the term "water-labile active ingredient" refers to an active ingredient that breaks down by water.

As active ingredients used in the present formulation, one or more components selected from, for example, nutritional tonics, antipyretic analgesics, antianxiety drugs, antidepressants, hypnotics, anticonvulsants, central nervous system agonists, cerebral circulation improving agents, antiepileptics, gastrointestinal agents, antiulcer agents, antiphlegm agents, antiemetics, respiratory accelerators, allergic agents, oral antihistamines, cardiotonics, antiarrhythmic agents, diuretics, blood pressure lowering agents, vasodilators, peripheral vasodilators, and antihyperlipidemic agents, cholestatic agents, antibiotics, antidiabetic agents, osteoporosis agents, anti-rheumatic agents, skeletal muscle relaxants, hormonal agents, alkaloidnarcotics, sulfa agents, anti-gout agents, anti-coagulants, anti-malignant agents, etc. are used.

Nutritional health agents include vitamin A, vitamin D, vitamin E (e.g., d-α-tocopherol acetate), vitamin B1 (e.g., dibenzoylthiamine, flusultiamine hydrochloride), vitamin B2 (e.g., riboflavin butyrate), vitamin B6 (e.g., pyridoxine hydrochloride), vitamin C (e.g., ascorbic acid, sodium L-ascorbate), vitamin B12 (e.g., hydroxocobalamin acetate, cyanocobalamin), minerals such as calcium, magnesium, iron, proteins, amino acids, oligosaccharides, herbal medicines, and the like. Antipyretic analgesics include, for example, aspirin, acetaminophen, ethenzamide, ibuprofen, diphenhydramine hydrochloride, dl-chlorpheniramine maleate, dihydrocodeine phosphate, noscapine, methylephedrine hydrochloride, phenylpropanolamine hydrochloride, caffeine, anhydrous, serapeptase, lysozyme chloride, tolfenamic acid, mefenamic acid, diclofenac sodium, flufenamic acid, salicylamide, aminopyrine, ketoprofen, indomethacin, bucolome, pentazocine, and the like.

Psychotropic drugs include, for example, chlorpromazine, reserpine, and the like. Anxiolytics include, for example, alprazolam, chlordiazepoxide, diazepam, and the like. Antidepressants include, for example, imipramine, maprotiline hydrochloride, amphetamine, and the like. Examples of hypnotic sedatives are estazolam, nitrazepam, diazepam, perrapine, phenobarbital sodium, and the like. Anticonvulsants include, for example, scopolamine hydrobromide, diphenhydramine hydrochloride, papaverine hydrochloride, and the like. Examples of central nervous system agonists are citicoline and the like. Examples of the cerebral metabolism improvement agent include meclofenixate hydrochloride and the like. Cerebral circulation improvement agents include, for example, vinpocetine. Antiepileptic agents include, for example, phenytoin, carbamazepine, and the like. The sympathomimetic agent includes, for example, isoproterenol hydrochloride. Gastrointestinal drugs include, for example, diastases, sugar-containing pepsins, lote extracts, cellulases AP3, lipases APs, healthy gastrointestinal digesters such as cinnamon oil, berberine chloride, resistant lactic acid bacteria, intestinal regulators such as bifidobacteria, and the like.

Antacids include, for example, magnesium carbonate, sodium bicarbonate, magnesium metasilicate aluminate, synthetic hydrotalcites, precipitated calcium carbonate, magnesium oxide, and the like. Anti-ulcer agents include, for example, lansoprazole, omeprazole, rabeprazole, famotidine, cimetidine, ranitidine hydrochloride, and the like. Antitussive expectorants include, for example, cloperastine hydrochloride, dextromeltophan hydrobromide, theophylline, potassium guaiacolsulfonate, guaifenesin, codeine phosphate, and the like. Antiemetic agents include, for example, diphenidol hydrochloride, metoclopramide, and the like. Respiratory promoters include, for example, levallorphan tartrate.

Bronchodilators include, for example, theophylline, salbutamol sulfate, and the like. Allergic drugs include amlexanox and ceratro dust. Dental oral agents include, for example, oxytetracycline, triamcinolone acetonide, chlorhexidine hydrochloride, lidocaine, and the like.

Antihistamines include, for example, diphenhydramine hydrochloride promethazine, isothipendyl hydrochloride, chlorpheniramine dl-maleate, and the like. Cardiotonics include, for example, caffeine, digoxin, and the like. Arrhythmia agents include, for example, procainamide hydrochloride, propranolol hydrochloride, pindolol, and the like. Diuretics include, for example, isosorpide, furosemide, hydrochlorothiazide, and the like. Blood pressure lowering agents include, for example, delapril hydrochloride, captopril hydrochloride, hydralazine hydrochloride, labetalol hydrochloride, manidipine hydrochloride, candesartan cilexetil, methyldopa, perindopril erbumin, and the like. Vasoconstrictors include, for example, phenylephrine hydrochloride.

Coronary vasodilators include, for example, carbochromen hydrochloride, molsidomine, perapamil hydrochloride, and the like. Peripheral vasodilators include, for example, cinnarizine. Agents for hyperlipidemia include, for example, cerivastatin sodium, simvastatin, pravastatin sodium, atorvastatin calcium hydrate, and the like. Biliary agents include, for example, dehydrocholic acid, trepiptone, and the like. Antibiotics include, for example, cefalexin, cefaclor, amoxicillin, pipmecillinam hydrochloride, cefotiam hexetil hydrochloride, cefadroxil, cefixime, cefditoren pivoxil, cefteram pivoxil, cefpodoxim iproxetil, and cefpodoxime iproxetil, ampicillin, cyclacin, nalidixic acid, synthetic antimicrobials such as enoxacin, monobactams such as sodium carmonam, penems, and carbapenem antibiotics.

Chemotherapeutic agents include, for example, sulfamethizole. Agents for diabetes include, for example, tolbutamide, voglibose, pioglitazone hydrochloride, glibenclamide, troglidazone, and the like. As an agent for osteoporosis, for example, ipriflavone and the like are mentioned. Skeletal muscle relaxants include methocarbamol and the like. As the antispasmodic agent, meclizine hydrochloride, dimenhydrinate, etc. are mentioned. Antirheumatic drugs include methotrexate and bucillamine. Hormonal agents include, for example, sodium liothyronine, dexmethasone sodium phosphate, prednisolone, oxendrone, leuprorelin acetate, and the like. Alkaloid narcotics include opium, morphine hydrochloride, tochon, oxycodone hydrochloride, opium hydrochloride alkaloid, and cocaine hydrochloride. Sulfa agents include, for example, sulfisomidine, sulfamethizole, and the like. Gout therapeutic agent includes, for example, allopurinol, colchicine, and the like. Anticoagulants include, for example, dicumarol. Antineoplastic agents include, for example, 5-fluorouracil, uracil, mitomycin, and the like.

These active ingredients can be used alone or in combination with other pharmaceuticals. In addition, these drugs are administered in a known appropriate amount as determined according to the disease, age, and the like of the patient.

It should be noted that active ingredients not only include compounds but also pharmaceutically acceptable salt of the compounds or their solvate.

The content of the active ingredient in the present formulation may be such that it produces a drug effect. Specifically, it is not more than 10% by weight, preferably between 0.001 and 10% by weight, more preferably not more than 5% by weight, more preferably between 0.005 and 5% by weight, particularly preferably not more than 1% by weight, very preferably between 0.01 and 1% by weight, with respect to the total amount of the formulation.

As an active ingredient in the present formulation, preferably, the compound represented by the formula (IA):

[Formula 3]

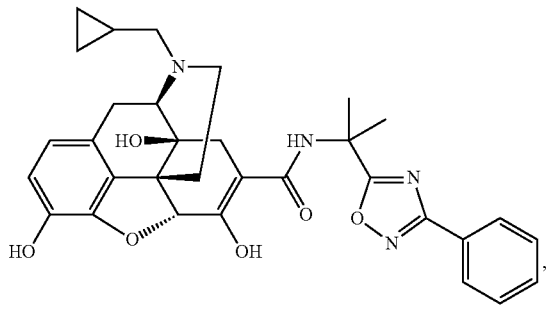

(IA)

or its pharmaceutically acceptable salts, or their solvate are used. It is preferably p-toluenesulfonic acid salt, acetate or hydrochloride of the compound represented by the formula (IA) or its solvate as an active ingredient, more preferably p-toluenesulfonic acid salt of the compound represented by the formula (IA) or its solvate as an active ingredient.

The formulation of compounds represented by the formula (IA), its pharmaceutically acceptable salts or their solvate, and p-toluenesulfonic acid salts of compounds represented by the formula (IA) or its solvate are disclosed in the International Publication No. 2006/126637 and International Publication No. 2012/063933.

The content of the compound represented by the formula (IA) in the present formulation, in particular, the compound p-toluenesulfonic acid salt represented by the formula (IA) or the solvate of the salt, may be in such amount as to produce a medicinal effect. Specifically, it is not more than 10% by weight, preferably between 0.001 and 10% by weight, more preferably not more than 5% by weight, more preferably between 0.005 and 5% by weight, particularly preferably 1% or less by weight, very preferably between 0.01 and 1% by weight, with respect to the total amount of the formulation.

In the present formulation, the upper limit of the median particle size of the active ingredient, which is also related to the median particle size with the active ingredient, is 10 μm or less, preferably 8 μm or less, and more preferably 5 μm or less. On the other hand, in the formulation of the present invention, the lower limit of the median particle size of the active ingredient is preferably 0.05 μm or more, and more preferably 0.1 μm or more, although there is no particular limitation.

The dose of p-toluenesulfonic acid salt of the compound represented by the formula (IA) in the formulation of the present invention should be set in consideration of the age, body weight, type and degree of disease, administration route, and the like of the patient.

The formulations contain excipients. Excipients have the highest percentage of inclusion among the additives of the formulations of the present invention. As excipients, excipients listed in the Japanese Pharmacopoeia, the Japanese Pharmaceutical Codex or the Japanese Pharmaceutical Excipients and the like can be used. Specifically, sugar alcohols such as D-mannitol, xylitol, sorbitol, maltitol, lactitol, oligosaccharide alcohols, xylose, glucose, fructose, maltose, lactose, sucrose (sucrose), isomerized sugar, syrup, purified sucrose, sucrose, granular purified sucrose, anhydrous lactose, granular sucrose•starch, and the like, hemi-digestive starch, sugar hydrate, powder sugar, crystalline cellulose, pullulan, ß-cyclodextrin, amino ethyl sulfonic acid, American powder; sodium chloride; sodium citrate; glycine; calcium gluconate; L-glutamine; tartrate; potassium hydrogen tartrate; ammonium carbonate; dextrin; calcium lactate; povidone; macrogol (polyethylene glycol) 1500; macrogol 4000; macrogol 6000; citric anhydride, DL-malate, sodium hydrogen phosphate, sodium dihydrogen phosphate, L-aspartate, sodium calmelose, sodium hydrous silicon, glycerophosphate, calcium glycerophosphate, calcium silicate, magnesium silicate, synthetic aluminium anhydride, wheat flour, wheat germ oil, rice flour, rice starch, cellulose acetate, titanium oxide, dihydroxy aluminium aminoacetate, calcium tertiary phosphate, talc, calcium carbonate magnesium carbonate; natural aluminum silicate; corn starch; corn starch granules; potato starch; hydroxypropyl cellulose; calcium hydrogenphosphate anhydride; calcium hydrophosphate granules, calcium dihydrogen phosphate and the like are included, preferably lactose and crystalline cellulose.

The content of excipients in the present formulation is 50-99.99 wt %, preferably 60-99.99 wt %, and more preferably 70-99.99 wt %, relative to the total amount of the formulations.

In the present formulation, the difference between the median particle size of the active ingredient and the median particle size of the excipient results in high content uniformity. That is, we found that the larger these differences, the smaller the standard deviation of the active ingredient content. That is, if the median particle size of the excipient is 15 times or more, preferably 17.5 times or more, and more preferably 20 times or more with respect to the median particle size of the active ingredient, the standard deviation of the active ingredient content within 5% or less, preferably 4% or less, and more preferably 3% or less. It is speculated that when the median particle size of excipients is large and the difference is large with respect to the active ingredient, composites can be formed with the active ingredient and excipients; moreover, by approximating the powder properties such as particle size, shape and bulk density of this composite to those of other additives, segregation between particles can be suppressed and the uniformity of the content of the active ingredient can be enhanced.

Content uniformity of the active ingredient in the drug product is generally assessed by the formulation uniformity test listed in the Japanese Pharmacopoeia. In addition, this evaluation is performed using values (judged values) calculated using the average content in addition to the standard deviation of individual content values. In the meantime, it was judged to be appropriate to evaluate only the degree of variance of the active ingredient using only the standard deviation of individual content values. When the standard deviation of the content value is 5% or less, it was generally considered preferable that the standard deviation of the active ingredient content is 5% or less because it meets the criteria of the formulation uniformity test.

When the active ingredient and excipient are mixed, and when the standard deviation of the active ingredient content in the drug product becomes more than 5%, it is possible to obtain a solid drug product in which the standard deviation of the active ingredient content in the drug product is 5% or less by mixing the excipient with the active ingredient using as the excipient that has a median particle size of 15 times or more with respect to the median particle size of the active ingredient. Also, by using an active ingredient with a median particle size of 15 fold or less relative to the median particle size of the excipients, and by mixing the active ingredient with excipients, it is possible to obtain solid formulations with a standard deviation of within 5% of the active ingredient content in the formulation.

That is, the present invention is a useful technique in obtaining solid formulations in which the standard deviation of the active ingredient content in the formulation is 5% or less for an active ingredient such that the standard deviation of the active ingredient content in the formulation is more than 5% when the active ingredient and excipient are mixed.

In the present formulation, the lower limit of the median particle size of the excipients, which is also related to the median particle size with the active ingredient, is 30 μm or more, preferably 45 μm or more, and more preferably 60 μm or more. On the other hand, the upper limit of the median particle size of the excipients is 350 μm or less, preferably 300 μm or less, and more preferably 250 μm or less. When multiple types of excipients are used, the standard deviation of the active ingredient content is 5% or less, preferably 4% or less, and more preferably 3% or less, if the median particle size of excipients with the largest median particle size is 15-fold or more, preferably 17.5-fold or more, and more preferably 20-fold or more with respect to the median particle size of the active ingredient. When using multiple types of excipients, preferably, the excipients with the largest median particle size and the active ingredient are firstly mixed, followed by other excipients and additives. Even if the amount of excipients with the largest particle size is small, the active ingredient itself can be mixed with a sufficient quantity of excipients to make the standard deviation of the active ingredient content in the formulation within 5%, preferably if the active ingredient content in the formulation is less than or equal to 10 wt %, more preferably less than or equal to 5 wt %, especially preferably less than or equal to 1 wt %.

The formulation may contain a disintegrating agent. As disintegrating agents, those listed in the Japanese Pharmacopoeia, the Japanese Pharmaceutical Codex or the Japanese Pharmaceutical Excipients and the like can be used. Specifically, cross-carmellose sodium, cross-povidone, carmellose calcium, carboxymethyl starch sodium, low-substituted hydroxypropyl cellulose, and the like are enumerated, and preferably cross-carmellose sodium.

The content of disintegrating agent in the formulation is 0.5 to 30 wt %, preferably 0.75 to 25 wt %, and more preferably 1 to 20 wt %, relative to the total amount of the formulation.

This formulation may contain a lubricant, and it is possible to use a lubricant listed in the Japanese Pharmacopoeia, the Japanese Pharmaceutical Codex or the Japanese Pharmaceutical Excipients, and the like. Specific examples include metal stearate, sucrose fatty acid ester, talc, hydrous silicon dioxide, and the like, preferably include metal stearate. Metal stearate includes magnesium stearate, calcium stearate, and the like, preferably includes magnesium stearate.

The content of the lubricant is usually 0.05 to 10 wt %, preferably 0.075 to 7.5 wt %, and more preferably 0.1 to 5 wt %, relative to the total amount of the formulation.

The present formulation may contain a coating agent and the coating agent listed in the Japanese Pharmacopoeia, the Japanese Pharmaceutical Codex or the Japanese Pharmaceutical Excipients and the like can be used. Specifically, hypromellose (hydroxypropyl methylcellulose), polyvinyl alcohol, ethyl cellulose, carmellose, sodium carmellose, hydroxyethyl cellulose, hydroxyethyl methylcellulose, PVA copolymer, ethyl acrylate-methyl methacrylate copolymer dispersion, aminoalkyl methacrylate copolymer, opadly, carboxyvinyl polymer, dry methacrylate copolymer, dimethylaminoethyl methacrylate-methyl methacrylate copolymer, stearyl alcohol, shellac, setanol, hydroxypropyl methylcellulose acetate succinate, hydroxypropyl methylcellulose phthalate, and a mixture of fumaric acid, stearic acid, and polyvinyl acetal diethylaminoacetate and hydroxypropyl methylcellulose, polyvinyl acetal diethylaminoacetate, polyvinyl alcohol, methacrylic acid copolymer, 2-methyl-5-vinylpyridine methylacrylate methacrylate copolymer, and the like are included, preferably hypromellose (hydroxypropyl methylcellulose).

The content of the coating agent in the present formulation is usually 0.1 to 10 wt %, preferably 0.25 to 7.5 wt %, and more preferably 0.5 to 5 wt %, relative to the total amount of the formulation.

Plasticizers and anti-coagulants may be included in the coating agent to efficiently perform the coating operation, and those listed in the Japanese Pharmacopoeia, the Japanese Pharmaceutical Codex, the Japanese Pharmaceutical Excipients or Japan's specifications and standards for food additives and the like can be used. Specific examples include macrogol 1000, macrogol 1500, macrogol 1540, macrogol 4000, macrogol 6000, macrogol 8000, macrogol 20000, macrogol 35000, and the like (polyethylene glycol with an average molecular weight of 1000 to 35000), glycerin fatty acid esters, sucrose fatty acid esters, castor oil, talc, and the like.

The formulation may contain dyes or colorants, and dyes listed in the Japanese Pharmacopoeia, the Japanese Pharmaceutical Codex or the Japanese Pharmaceutical Excipients and the like can be used. Dyes can be contained both in tablets and in coating layers. Dyes specifically include iron oxide, tar dyes and natural dyes. Iron oxides include iron tridioxide, iron yellow oxide, yellow iron trioxide, black iron oxide, and the like. Tar dyes include edible yellow No. 4 aluminum lakes, edible blue No. 1 aluminum lakes, edible red No. 3 aluminum lakes, edible blue No. 1, edible blue No. 2, edible yellow No. 4, edible yellow No. 5, edible red No. 102, edible red No. 2, edible red No. 3, etc. Natural pigments include turmeric extract, 8-carotene, carotene solution, copper chlorophyllin sodium, copper chlorophyll, powdered green leaf extract of red wheat, dry powder of bare green leaf blue juice, and extract of bare wheat green leaf.

The formulation may further contain additives other than those listed above, if necessary, and additives listed in the Japanese Pharmacopoeia, the Japanese Pharmaceutical Codex, the Japanese Pharmaceutical Excipients or Japan's specifications and standards for food additives can be used.

Also, the content of these additives may be at any rate. Additive agents other than those described above specifically include binders, flavors, fluidizers, flavoring agents, flavoring agents, and the like.

Specific examples of the binder include hydroxypropyl cellulose, corn starch, alphalized starch, portion alphalized starch, gum arabic, gum arabic powder, gelatin, agar, dextrin, pullulan, polyvinylpyrrolidone, polyvinyl alcohol, crystalline cellulose, methylcellulose, ethyl cellulose, carboxymethyl ethyl cellulose, carmelose, sodium carmelose, hydroxy ethyl cellulose, hydroxy ethyl methylcellulose, hydroxy propyl cellulose, hypromellose, and the like.

Flavoring agents include orange essence, orange oil, caramel, camphor, silkworm oil, spearmint oil, stroberry essence, chocolate essence, cherry flavor, spruce oil, pine oil, hacka oil, vanilla flavor, bitter essence, fruit flavor, peppermint essence, mix flavor, mint flavor, menthol, lemon powder, lemon oil, rose oil, and the like.

Fluidizing agents specifically include hydrous silicon dioxide, light silicic anhydride, crystalline cellulose, synthetic aluminum silicate, talc, and the like.

Taste correction agents specifically include aspartame, sucralose, glycine, sodium chloride, magnesium chloride, hydrochloric acid, dilute hydrochloric acid, citric acid and its salts, citric anhydrous, L-glutamic acid and its salts, succinic acid and its salts, acetic acid, tartaric acid and its salts, sodium bicarbonate, fumaric acid and its salts, malic acid and its salts, glacial acetic acid, disodium inosinate, honey, and the like.

The present formulation may be a solid formulation. Specifically, granules, fine granules, tablets, powders, capsules, pills, etc. may be used, preferably granules or tablets.

The manufacturing method of granules of the present formulation is not particularly limited as long as it is a manufacturing method with good content uniformity of the active ingredient and no decomposition of the active ingredient, but specifically, it is a method of mixing additives such as active ingredient, disintegrating agent, excipient, etc. to granulate the mixed powder after the production, and it is a dry granulation method, fracture granulation method, and melt granulation method, preferably by compression forming without using water. The granules can also be coated by coating the granules with a coating agent after the granules are made. V-type mixing machines and container blenders can be used as machines to mix active ingredients, additives, etc. Also, dry fracturing granulating, fracturing granulators, and melt extrusion granulators can be used as the granulating machines.

The manufacturing method of the tablet of the present formulation is not particularly limited as long as the formulation method has good content uniformity of the active ingredient and does not degrade the active ingredient, but specifically, it is a direct compression method in which an additive such as an active ingredient, a disintegrating agent, or an excipient is mixed to produce a mixed powder, and then the mixed powder is tableted by a tablet-pressor. V-type mixing machines and container blenders can be used as machines to mix active ingredients, additives, etc. Further, as the compression machine, a single compression machine, a rotary compression machine, or the like can be used.

If the manufacturing method of the present formulation is a manufacturing method characterized by including the process of mixing the excipient having a median particle size of 10 µm or less of the active ingredient and a median particle size of 30 µm or more of the excipient in the formulation and a median particle size of 15 times or more with respect to the median particle size of the active ingredient, the standard deviation of the active ingredient content in the formulation can be 5% or less.

If the manufacturing method of the present formulation is a manufacturing method characterized by including the process of mixing the excipient having a median particle size of 8 µm or less of the active ingredient and a median particle size of 45 µm or more of the excipient in the formulation and a median particle size of 17.5 times or more with respect to the median particle size of the active ingredient, the standard deviation of the active ingredient content in the formulation can be 5% or less.

If the manufacturing method of the present formulation is a manufacturing method characterized by including the process of mixing the excipient having a median particle size of 5 µm or less of the active ingredient and a median particle size of 60 µm or more of the excipient in the formulation and a median particle size of 20 times or more with respect to the median particle size of the active ingredient, the standard deviation of the active ingredient content in the formulation can be 5% or less.

If the manufacturing method of the present formulation, wherein the active ingredient content can be 10 wt % or less, is a manufacturing method characterized by including the process of mixing the excipient having a median particle size of 10 µm or less of the active ingredient and a median particle size of 30 µm or more of the excipient in the formulation and a median particle size of 15 times or more with respect to the median particle size of the active ingredient, the standard deviation of the active ingredient content in the formulation can be 5% or less.

If the manufacturing method of the present formulation, wherein the active ingredient content can be 5 wt % or less, is a manufacturing method characterized by including the process of mixing the excipient having a median particle size of 8 µm or less of the active ingredient and a median particle size of 45 µm or more of the excipient in the formulation and a median particle size of 17.5 times or more with respect to the median particle size of the active ingredient, the standard deviation of the active ingredient content in the formulation can be 4% or less.

If the manufacturing method of the present formulation, wherein the active ingredient content can be 1 wt % or less, is a manufacturing method characterized by including the process of mixing the excipient having a median particle size of 5 µm or less of the active ingredient and a median particle size of 60 µm or more of the excipient in the formulation and a median particle size of 20 times or more with respect to the median particle size of the active ingredient, the standard deviation of the active ingredient content in the formulation can be 3% or less.

If the manufacturing method of the present formulation, wherein the active ingredient content can be 10 wt % or less in the formulation, is a manufacturing method characterized by including the process of mixing the excipient having a median particle size of 10 µm or less of the active ingredient and a median particle size of 30 µm or more of the excipient in the formulation and (i) the process of mixing the active ingredient, and the excipient of a median particle size of 20 times or more with respect to the median particle size of the active ingredient, (ii) the process of compressively forming the mixture by direct compression or dry granulation method, the standard deviation of the active ingredient content in the formulation can be 5% or less.

If the manufacturing method of the present formulation, wherein the active ingredient content can be 5 wt % or less in the formulation, is a manufacturing method characterized by including the process of mixing the excipient having a median particle size of 8 μm or less of the active ingredient and a median particle size of 45 μm or more of the excipient in the formulation and (i) the process of mixing the active ingredient, and the excipient of a median particle size of 17.5 times or more with respect to the median particle size of the active ingredient, (ii) the process of compressively forming the mixture by direct compression or dry granulation method, the standard deviation of the active ingredient content in the formulation can be 4% or less.

If the manufacturing method of the present formulation, wherein the active ingredient content can be 1 wt % or less in the formulation, is a manufacturing method characterized by including the process of mixing the excipient having a median particle size of 5 μm or less of the active ingredient and a median particle size of 60 μm or more of the excipient in the formulation and (i) the process of mixing the active ingredient, and the excipient of a median particle size of 20 times or more with respect to the median particle size of the active ingredient, (ii) the process of compressively forming the mixture by direct compression or dry granulation method, the standard deviation of the active ingredient content in the formulation can be 3% or less.

The manufacturing method of the present formulation allows the production of solid formulations with standard deviations of 5% or less and preferably 3% or less of the active ingredient content in the formulation.

The prescriptions of present formulations are specifically solid formulations containing water-labile compounds, their pharmaceutically acceptable salts or their solvates as active ingredients and excipients, with an active ingredient content of 10 wt % or less and a standard deviation of the active ingredient content within 5%, preferably solid formulations containing water-labile compounds or their solvates as active ingredients and excipients, with an active ingredient content of 5 wt % or less and a standard deviation of the active ingredient content within 4%, and more preferably solid formulations containing water-labile compounds or their solvates as active ingredients and excipients, with an active ingredient content of 1 wt % or less and a standard deviation of the active ingredient content within 3%.

The prescriptions of present formulations are specifically solid formulations containing water-labile compounds, their pharmaceutically acceptable salts or their solvates as active ingredients, and 50 to 99.99 wt % excipients, with an active ingredient content of 10 wt % or less and a standard deviation of the active ingredient content within 5%, preferably solid formulations containing water-labile compounds or their solvates as active ingredients and 60 to 99.99 wt % excipients, with an active ingredient content of 5 wt % or less and a standard deviation of the active ingredient content within 4%, and more preferably solid formulations containing water-labile compounds or their solvates as active ingredients and 70 to 99.99 wt % excipients, with an active ingredient content of 1 wt % or less and a standard deviation of the active ingredient content within 3%.

The prescriptions of present formulations are specifically solid formulations containing water-labile compounds, their pharmaceutically acceptable salts or their solvates as active ingredients, and excipients, with an active ingredient content of 10 wt % or less and a standard deviation of the active ingredient content within 5%, preferably solid formulations containing water-labile compounds or their solvates as active ingredients and excipients, with an active ingredient content of 5 wt % or less and a standard deviation of the active ingredient content within 4%, and more preferably solid formulations containing water-labile compounds or their solvates as active ingredients and excipients, with an active ingredient content of 1 wt % or less and a standard deviation of the active ingredient content within 3%.

The prescriptions of present formulations are specifically solid formulations containing water-labile compounds, their pharmaceutically acceptable salts or their solvates as active ingredients, and 50 to 99.99 wt % excipients, with an active ingredient content of 10 wt % or less and a standard deviation of the active ingredient content within 5%, preferably solid formulations containing water-labile compounds or their solvates as active ingredients and 60 to 99.99 wt % excipients, with an active ingredient content of 5 wt % or less and a standard deviation of the active ingredient content within 4%, and more preferably solid formulations containing water-labile compounds or their solvates as active ingredients and 70 to 99.99 wt % excipients, with an active ingredient content of 1 wt % or less and a standard deviation of the active ingredient content within 3%.

The prescriptions of present formulations are specifically solid formulations containing the salts of p-toluenesulfonic acid salt, or a solvate thereof of the compound represented by the formula (IA) as the active ingredient and excipients, and the active ingredient content is 10 wt. % or less, and a standard deviation of the active ingredient content within 5%, preferably solid formulations containing the salts of p-toluenesulfonic acid salt, or a solvate thereof of the compound represented by the formula (IA) as the active ingredient and excipients, and the active ingredient content is 5 wt. % or less, and the standard deviation of the active ingredient content within 4%, more preferably solid formulations containing the salts of p-toluenesulfonic acid salt, or a solvate thereof of the compound represented by the formula (IA) as the active ingredient and excipients, and the active ingredient content is 1 wt. % or less, and the standard deviation of the active ingredient content within 3%.

The prescriptions of present formulations are specifically solid formulations containing the salts of p-toluenesulfonic acid salt, or a solvate thereof of the compound represented by the formula (IA) as the active ingredient and 50-99.99 wt % excipients, and the active ingredient content is 10 wt. % or less, and a standard deviation of the active ingredient content within 5%, preferably solid formulations containing the salts of p-toluenesulfonic acid salt, or a solvate thereof of the compound represented by the formula (IA) as the active ingredient and 60-99.99 wt % excipients, and the active ingredient content is 5 wt. % or less, and the standard deviation of the active ingredient content within 4%, more preferably solid formulations containing the salts of p-toluenesulfonic acid salt, or a solvate thereof of the compound represented by the formula (IA) as the active ingredient and 70-99.99 wt % excipients, and the active ingredient content is 1 wt. % or less, and the standard deviation of the active ingredient content within 3%.

As the tablet shape, any shape can be adopted, and specifically, it can be a tablet with a round, oval, spherical, rod-shaped, or doughnut-shaped shape. It may also be a stacked tablet, a nucleated tablet, etc., preferably a single-layer tablet with a convenient manufacturing method is preferable. Furthermore, marks, letters, and the like may be inscribed to improve the discrimination, as well as allocation lines for division.

EXAMPLES

The present invention will be explained in more detail below by way of Examples, Comparative Examples and Reference Examples, but these do not limit the present invention.

(1) Effect of median particle size of active ingredients and excipients on content uniformity.

The effect of the median particle size of the active ingredients and excipients on the content uniformity of the active ingredients was studied. Content uniformity represents whether the active ingredient is contained without segregation in formulations such as granules and tablets. As active ingredients, p-toluenesulfonic acid salt of compounds of the formula (IA) and D-mannitol (made by Roquette or Merck) were used as excipients. After mixing powders formulated with active ingredients and excipients of various median particle sizes in Table 1 in wt. % of Table 1, the active ingredient content of the compacted tablets was determined by the following method and their standard deviations were determined from the results:

The tablets of Examples 1 and 2 and Comparative Example 1 were prepared under the following conditions: 3.906 g p-toluenesulfonic acid salt (3 g as a compound of the formula (IA)) of the compound of the formula (IA) and 2366 g D-mannitol, 600 g of low-substituted hydroxypropyl cellulose, are sieved three times with a wire mesh of 30 mesh followed by mixing at 37 rpm for 33 min using a V-type mixing machine (effective volume 8 L). To the mixture add 30 g of magnesium stearate sieved through a 30-mesh wire mesh and mix at 37 rpm for 5 minutes. The resulting mixtures were also compacted to produce tablets using a rotary compression machine (Kikuchi Manufacturing RTM-S30K-2 S type).

The tablets used in Example 3 were produced under the following conditions: p-toluenesulfonic acid salt 234.4 g of the compound of the formula (IA) (180 g as compound of the formula (IA)) and 96,430 g of D-mannitol, 1,080 g of sodium cross-carmellose are sieved once with a 30-mesh wire mesh followed by mixing at 20 rpm for 27 min using a V-type mixing machine (effective volume 273 L). To the mixture add 540 g of magnesium stearate sieved through a 30-mesh wire mesh and mix at 20 rpm for 2.7 minutes. The resulting mixtures were also compacted to produce tablets using a rotary compression machine (Kikuchi Manufacturing LIBRA2).

The median particle size (volume-averaged particle size) of the active ingredient was determined using a particle size measuring machine made by HELOS(H1086) & ROSOS (manufactured by Nippon Laser) with a focal length of 100 mm and a dispersive pressure of 2 bars under the following conditions:
HELOS (Laser Diffraction Unit)
Type: HELOS(H1086)
Lens: R3
Measuring range: 0.5-175 µm
Trigger condition: 2 s-100 ms-k15-0.5%-0.2%
Calculation mode: HRLD (5.3.0.0)
RODOS (Dispersing System)
Feeder: VIBRI
Dispersion pressure: 2.00 bar
Degree of vacuum: 100 mbar
Feeding: 50.00%
Rotation: 30.00%
Density: 1.00 g/cm$^3$
Shape counting: 1.00

In addition, the median particle size (volume-averaged particle size) of the excipients was evaluated under the conditions of a focal length of 100 mm and a dispersive pressure of 3 bar using a particle size measuring machine of HELOS(H1086) & ROSOS (manufactured by Nippon Laser).
HELOS (Laser Diffraction Unit)
Type: HELOS(H1086)
Lens: R5
Measuring range: 0.5-875 µm
Trigger condition: 2 s-100 ms-conc-1.0%-1.0%
Calculation mode: HRLD (5.8.0.0)
RODOS (Dispersing System)
Feeder: VIBRI
Dispersion pressure: 3.00 bar
Degree of vacuum: 134 mbar
Feeding: 45.00%
Rotation: 20.00%
Density: 1.00 g/cm$^3$
Shape counting: 1.00

(Determination of the Standard Deviation of the Content)

In Examples 1, 2 and Comparative Example 1, samples were taken out of 10 tablets each for a total of 40 tablets during the compression process at regular intervals for a total of 4 times, including at the start and end of compression, and their contents were determined by the test method described below.

In Example 3, samples were drawn from three tablets and 75 tablets in total at regular intervals for a total of 25 tablets during the compression process, including at the start and end of compression, respectively, and the contents of these tablets were measured by the test method described below.

The method for determination of the content of the formula (IA) compounds of the active ingredients was determined by the HPLC method (wavelength: 240 nm, column: L-column ODS (filler 5 µm, 4.6×250 mm, manufactured by the Chemical Assessment and Research Organization), column temperature: 45° C., mobile phase: a mixture of 20 mmol/L phosphate buffer solution/acetonitrile (13:7) in pH5.5, flow rate: 1.0 mL/min.

(Result)

TABLE 1

| | | Example 1 | Example 2 | Example 3 | Comparative Example 1 |
|---|---|---|---|---|---|
| Content in the formulation (wt %) | active ingredient* | 0.13 | 0.13 | 0.22 | 0.13 |
| | D-mannitol | 78.87 | 78.87 | 89.28 | 78.87 |
| | Low substituted hydroxypropyl cellulose | 20.0 | 20.0 | — | 20.0 |
| | Croscarmellose sodium | — | — | 10.0 | — |
| | Magnesium stearate | 1.0 | 1.0 | 0.5 | 1.0 |
| | Total | 100.0 | 100.0 | 100.0 | 100.0 |
| Median particle size(µm) | D-mannitol | 91.9 | 91.9 | 62.5 | 91.9 |
| | Active ingredient | 4.3 | 3.0 | 3.3 | 9.9 |
| D-mannitol/active ingredient particle size ratio | | 21.3 | 30.6 | 18.9 | 9.3 |

TABLE 1-continued

| | | Example 1 | Example 2 | Example 3 | Comparative Example 1 |
|---|---|---|---|---|---|
| Content of the active ingredient (%) | Average | 99.7 | 99.7 | 98.8 | 99.1 |
| | Standard deviation | 1.9 | 1.2 | 0.8 | 6.1 |

*Described as the amount of p-toluenesulfonic acid salt of the formula (IA) compound In Example 3, wherein the ratio of the median particle size of the active ingredient and D-mannitol was 18.9, the standard deviations of the active ingredient contents were 0.8% and the standard deviation was 5% or less. The ratio of the median particle size of the active ingredient and D-mannitol in Examples 1 and 2 was greater than 18.9 in Example 3, although the standard deviation of the content was less than 5% for both formulations. On the other hand, the ratio of the median particle size of the active ingredient and D-mannitol in Comparative Example 1 was less than 10, the standard deviation of the content became greater than 5%, and the content uniformity was low. Therefore, it was revealed that the standard deviation of the content became 5% or less, when the median particle size of the excipient with respect to the active ingredient was 15 times or more.

INDUSTRIAL APPLICABILITY

By mixing the active ingredient, and excipients with a median particle size of 15 times or more, preferably 20 times or more, relative to the median particle size of the active ingredient, solid formulations with good content uniformity can be produced, e.g., tablets, granules, powders and capsules. Since the manufacturing method of the present formulation is not cumbersome, the working efficiency of the formulation production is also high.

The invention claimed is:

1. A process for manufacturing a solid formulation, comprising:
    a step of mixing particles having a median particle size of 10 μm or less of a compound represented by formula (IA),

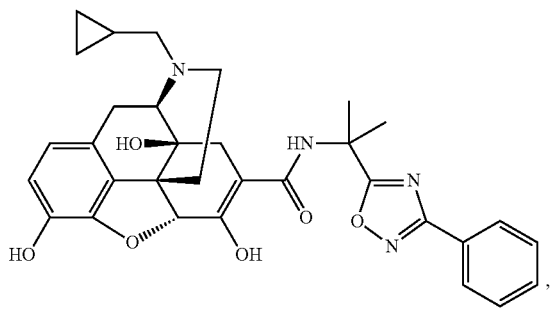

(IA)

its pharmaceutically acceptable salt, or a solvate thereof, as an active ingredient, with particles having a median particle size of 30 μm or more of an excipient to obtain a mixture, wherein the median particle size of the particles of the excipient is 15 times or more than the median particle size of the particles of the active ingredient in the mixture,
    a step of compression molding the mixture, and
    a step of determining a content of the active ingredient during the step of compression molding the mixture to obtain the solid formulation,
    wherein the standard deviation of the content of the active ingredient in the solid formulation is 5% or less, and
    wherein the content of the active ingredient in the solid formulation is 0.01 to 1% by weight.

2. The process for manufacturing a solid formulation according to claim 1,
    wherein the step of compression molding the mixture is by a direct compression method or a dry granulation method.

3. The process for manufacturing a solid formulation according to claim 1, wherein the median particle size of the particles of the excipient is 20 times or more than the median particle size of the particles of the active ingredient.

4. The process for manufacturing a solid formulation according to claim 1, wherein the standard deviation of the content of the active ingredient in the solid formulation is 3% or less.

5. The process for manufacturing of a solid formulation according to claim 1, wherein the content of the excipient in the solid formulation is 50 to 99.99% by weight.

6. The process for manufacturing a solid formulation according to claim 5, wherein the content of the excipient in the solid formulation is 60 to 99.99% by weight.

7. The process for manufacturing a solid formulation according to claim 5, wherein the content of the excipient in the solid formulation is 70 to 99.99% by weight.

8. The process for manufacturing a solid formulation according to claim 1, wherein the median particle size of the particles of the active ingredient is 8 μm or less.

9. The process for manufacturing a solid formulation according to claim 1, wherein the median particle size of the particles of the active ingredient is 5 μm or less.

10. The process for manufacturing a solid formulation according to claim 1, wherein the median particle size of the particles of the excipient is 45 μm or more.

11. The process for manufacturing a solid formulation according to claim 1, wherein the median particle size of the particles of the excipient is 60 μm or more.

12. The process for manufacturing a solid formulation according to claim 1, wherein the median particle size of the particles of the active ingredient is 5 μm or less, the median particle size of the particles of the excipient is 60 μm or more, the median particle size of the particles of the excipient is 20 times or more than the median particle size of the particles of the active ingredient, and wherein the standard deviation of the content of the active ingredient in the solid formulation is 3% or less.

13. The process for manufacturing a solid formulation according to claim 12, wherein the step of compression molding the mixture is by a direct compression method or a dry granulation method.

14. The process for manufacturing a solid formulation according to claim 1, wherein the active ingredient is a p-toluene sulfonic acid salt, acetate or hydrochloride salt of the compound represented by the formula (IA), or a solvate of the salt.

15. The process for manufacturing a solid formulation according to claim 1, wherein the excipient is a sugar or a sugar alcohol.

16. The process for manufacturing a solid formulation according to claim 15, wherein the excipient is D-mannitol.

17. The process for manufacturing a solid formulation according to claim 1, wherein the solid formulation is at least one formulation selected from the group consisting of a tablet, a granule, a powder and a capsule.

18. A solid formulation produced by the process for manufacturing, according to claim 1.

* * * * *